(12) United States Patent
Ivancev et al.

(10) Patent No.: US 6,589,275 B1
(45) Date of Patent: Jul. 8, 2003

(54) STENT DEVICE

(75) Inventors: Krasnodar Ivancev, Lund (SE); Erik Edelbo Rasmussen, Slagelse (DK)

(73) Assignee: William Cook Eurpoe ApS, Bjaeverskov (DK)

( * ) Notice: Subject to any disclaimer, the term of this patent is extended or adjusted under 35 U.S.C. 154(b) by 0 days.

(21) Appl. No.: 09/622,326

(22) PCT Filed: Feb. 24, 1999

(86) PCT No.: PCT/DK99/00078

§ 371 (c)(1),
(2), (4) Date: Oct. 13, 2000

(87) PCT Pub. No.: WO99/43272

PCT Pub. Date: Sep. 2, 1999

(30) Foreign Application Priority Data

Feb. 25, 1998 (DK) ................................................ 0256/98

(51) Int. Cl.⁷ ................................................ A61F 2/06
(52) U.S. Cl. ........................ 623/1.15; 623/1.13; 623/1.2
(58) Field of Search ............... 623/1.15, 1.16, 623/1.17, 1.2, 1.13, 1.51

(56) References Cited

U.S. PATENT DOCUMENTS

| | | | |
|---|---|---|---|
| 5,104,404 A | * | 4/1992 | Wolff ........................ 623/1.16 |
| 5,443,499 A | * | 8/1995 | Schmitt ...................... 623/1.13 |
| 5,776,161 A | * | 7/1998 | Globerman .................. 606/192 |
| 5,897,589 A | | 4/1999 | Cottenceau et al. |
| 5,957,949 A | * | 9/1999 | Leonhardt et al. ........... 606/108 |
| 6,033,433 A | * | 3/2000 | Ehr et al. .................... 623/1.16 |
| 6,036,723 A | * | 3/2000 | Anidjar et al. ............... 623/1.13 |
| 6,146,403 A | * | 11/2000 | St. Germain ................. 606/195 |
| 6,159,239 A | * | 12/2000 | Greenhalgh ................. 623/1.13 |
| 6,190,406 B1 | * | 2/2001 | Duerig et al. ............... 623/1.15 |
| 6,221,102 B1 | * | 4/2001 | Baker et al. ................. 623/1.13 |
| 6,253,443 B1 | * | 7/2001 | Johnson .................. 219/121.72 |
| 6,270,524 B1 | * | 8/2001 | Kim ........................... 606/194 |
| 6,280,466 B1 | * | 8/2001 | Kugler et al. ............... 623/1.12 |
| 6,325,821 B1 | * | 12/2001 | Gaschino et al. ........... 606/194 |
| 6,325,826 B1 | * | 12/2001 | Vardi et al. ................. 623/1.15 |
| 6,428,570 B1 | * | 8/2002 | Globerman .................. 623/1.15 |
| 2001/0044648 A1 | * | 11/2001 | Wolinsky et al. ........... 623/1.15 |
| 2001/0044649 A1 | * | 11/2001 | Vallana et al. .............. 623/1.15 |

FOREIGN PATENT DOCUMENTS

| | | |
|---|---|---|
| EP | 0335341 | 3/1992 |
| EP | 0539237 | 4/1993 |
| EP | 0480667 | 3/1996 |
| EP | 0712614 | 5/1996 |
| EP | 0818184 | 1/1998 |
| WO | 9641592 | 12/1996 |

\* cited by examiner

*Primary Examiner*—Rodney M. Lindsey
(74) *Attorney, Agent, or Firm*—Richard J. Godlewski

(57) ABSTRACT

A stent device (1) constructed from several consecutively arranged cylindrical spring member stents (4) interconnected by at least three resilient connecting members (5) that are firmly fastened to arm sections (6) at a distance from the elbow sections (7) of the stents (4). A graft (2) includes graft material (2) affixed to the stent device (1).

11 Claims, 3 Drawing Sheets

STENT DEVICE

FIELD OF THE INVENTION

The present invention relates to a medical devices and more particularly to a stent having at least one tubular member which has a longitudinal direction and comprises several longitudinally consecutive cylindrical spring members interconnected by connecting members, the individual cylindrical spring members each being an endless wire of a zigzag configuration having arm sections extending between elbow sections, and the tubular member being self-expanding from a radially compressed state with a relatively small diameter to a state with a larger diameter.

Such a stent device is known from EP 0 480 667. The cylindrical spring members constructed from an endless wire of a zigzag configuration are commonly called Z-stents sold by Cook Incorporated, Bloomington, Ind. or Gianturco stents, and they have proved to be very applicable for percutaneous transluminal insertion in a vessel in a radially compressed state and subsequent release and self-expansion at the desired site in the vessel in the vascular system. These stents can be compressed to a very compact state with an advantageously small diameter during insertion while retaining a strong self-expanding effect. In the known stent device, two cylindrical spring members (Z-stents) may be arranged at either end of a graft, and they may be interconnected by means of a single rigid bar extending in parallel with the longitudinal direction of the tubular member from an elbow section on one stent to an elbow section on the other stent. This stent device is suitable for cutting off an aneurysm, the two stents being arranged in the healthy vessel on either side of the aneurysm and pressing the graft out towards the vessel wall so that the aneurysm is cut off from the vessel.

It is possible to join several stents into long stent devices, but it may be difficult to obtain sufficient flexibility in the stent device for the insertion along curved vessel paths to perform suitably without problems. In a stent device invented by Chuter, see EP 0 539 237, several Z-stents are joined by providing the elbow sections with eyes in which a bar with thickened end sections is inserted. The bar permits the eyes to be displaced away from each other until they are stopped by the end sections so that one stent can be turned in an angular direction in relation to the other. At long-term implantation, however, the device may perhaps become damaged due to wear as a consequence of stent movements caused by the persistent pulsating loadings occurring in blood vessels.

Other prior-art stent devices are balloon-expandable and have several stent bodies joined by connecting members. Such devices have no actual resilient effect and depend fully on inflation of the balloon to be dilated to the correct diameter for fastening to the vessel wall to become suitable. During a period of time, the vessel geometry may change and negatively affect the fastening of the rigid, balloon-expandable stent body.

As an example of such non-self-expandable stent device can be mentioned EP 0 335 341, which provides joining of several stents by means of connecting members extending approximately in the circumferential direction between elbow sections on two adjacent stents. In the expanded state, this device has no particular longitudinal rigidity.

As another example of a non-self-expanding stent device can be mentioned EP 0 712 614, in which a graft is fastened to the vessel at either end by means of a stent formed by wave-shaped annular wires, the apex areas of which are interconnected by means of connecting members extending in the longitudinal direction of the tubular member. The fastening of the connecting members to the apex areas and the wave shape of the annular wires prevent a force acting axially on an annular wire from being transferred to a more remote annular wire, and at the same time the problems are further increased because an axial compression leads to local expansion of the diameter of the tubular member. At long-term placing in a vessel, some of the annular wires may be displaced in the longitudinal direction of the vessel in relation to others of the annular wires, while the intermediate annular wire(s) is/are slowly deformed to a larger diameter, and the vessel wall locally yields and grows to a correspondingly larger diameter. Furthermore, the two stents are not interconnected, and thus one graft end may migrate in relation to the other graft end. Moreover, the balloon-expandable stents suffer from the disadvantage that the flow through the vessel is completely cut off while the balloon is inflated for expansion of the stent.

It is a problem of the known stent devices that they are either too yielding to radial pressure or too rigid to permit bending of the longitudinal axis of the tubular member. A suitable rigidity to radial pressure is of importance to obtain the primary effect of keeping the vessel lumen open, while bending flexibility is important during the transluminal insertion of the device, when the highest possible bending flexibility is desired to prevent frictional locking against the vessel wall in areas with strong vessel curves. The desire for high bending flexibility may also be relevant to the properties in the implanted state, where the device may inflict injuries on the vessel if the bending rigidity is too great.

SUMMARY OF THE INVENTION

It is an object of the invention to provide a stent device that fulfils the desires of a suitable rigidity to radial pressure and a suitably high bending flexibility even when many consecutive stents are interconnected. It is further an object to provide a stent device that has a smaller tendency towards migration in the vessel over a long period following implantation than the prior-art devices.

In view thereof the stent device according to the present invention is characterized in that between the cylindrical spring member and the succeeding cylindrical spring member in the longitudinal direction there are at least three resilient connecting members firmly fastened to the arm sections of the cylindrical spring members at a distance from the elbow sections.

By fastening the resilient connecting members to the arm sections at positions at a distance from the elbow sections, the connecting members become longer, and the greater length reduces the rigidity of the connecting members to transverse deflection. When the tubular member is curved, the connecting members on the inside of the curve can more easily deflect with simultaneous reduction of the distance between the two nearest cylindrical spring members (in the following also called Z-stents). Mounting of the connecting member a distance inwards on the arm section provides the advantage that both the associated elbow sections become free to deflect in relation to the connecting member, which gives the Z-stent a more uniform deformation course in which the elbow section facing away from the connecting member is prevented from deflecting strongly radially outwards, which might otherwise result in an undesirable point load on the vessel wall.

It is important that the ends of the connecting members are firmly fastened to the arm sections. This reduces the long-term wear damage to the stent material, and the connection between the interconnected arm sections becomes rigid so that an axially directed pressure influence on a Z-stent is transmitted to the succeeding Z-stents via the pressure-transmitting connecting members. This latter effect is very important to reduce or prevent migration of stents after implantation. If a vessel wall area begins to yield at a stent in the stent body and to lose its grip thereon, for example as a consequence of a persistent pulsating blood pressure from only one side of the stent device, displacement of the stent in the longitudinal direction of the vessel is prevented by means of the pressure-rigid connecting members to the succeeding stent. Thus, the entire tubular member with the many joined stents assists in keeping all the stents in place, and longitudinal influences on the vessel wall are distributed over the length of the entire tubular member.

As the cylindrical spring members are self-expanding, it is no problem at the implantation that the tubular member comprises many spring members, since separate balloon expansion of the members is not needed. This is especially advantageous when the stent device comprises a tubular graft, as it can be supported over its, entire length by spring members located at short distance from each other. The stent device according to the invention is well suited for endovascular repair of vessel anomalies, because it is simple to introduce and place at the desired site and has a strong vessel-opening effect, and at long-term or permanent implantation the device has only a minor tendency towards migration and injury of the vessel.

In a preferred embodiment, the resilient connecting members extend obliquely in relation to the longitudinal direction when the tubular member is in its uncompressed state with the larger diameter. The oblique course helps to keep the lumen in the tubular member open, partly because the spring members are affected in both the circumferential and the longitudinal directions, and partly because the connecting members curve slightly outwards due to the tubular shape of the device and seek to keep the tubular member open when it is influenced by an axially directed load. Moreover, the oblique course allows transmission of torsional influences throughout the tubular member.

To obtain relatively uniform properties at bending of the tubular member in different directions, the individual connecting member is preferably connected to the associated arm sections to extend in the same direction as the arm sections, so that the connecting members and the arm sections extend along several substantially helical courses in the tubular member when the tubular member is in its uncompressed state with the larger diameter. Thus, the individual connecting member extends in the same arcuate direction as the two associated arm sections, which also imparts great pressure rigidity to the tubular member. Furthermore, all the helical courses preferably turn in the same direction, as this simplifies the manufacture of the tubular member.

The ability of the device to stay open is best when the connecting members between adjacent cylindrical members are evenly distributed in the circumferential direction. As there are at least three connecting members, there is thus at the most 120° in the circumferential direction between two connecting members, and when the connecting members furthermore extend obliquely as mentioned above, bending in only one direction cannot lead to kinking of the tubular member.

In one embodiment having a particularly high bending flexibility, on the individual cylindrical member the connecting members to the preceding cylindrical member are fastened to arm sections which are positioned offset at least one arm section from the arm sections to which the connecting members to the succeeding cylindrical spring member are fastened to said individual cylindrical spring member. This means that both in the circumferential and the longitudinal directions on both sides of a connecting member there is a free elbow section which can be moved closer to the adjacent stent on the inside of the curve and further away from the adjacent stent on the outside when the tubular member is bent.

In order to obtain symmetrical and thus uniform deformation patterns of the spring members to the extent possible, the connecting members may be fastened substantially at the middle of the arm sections.

In one embodiment, the connecting members are made of a more flexible spring material, preferably annealed stainless steel, than the cylindrical spring members. This allows the connecting members to perform greater deflections at bending of the tubular member so that the spring members on the inside of the bend can more easily be moved towards each other.

The stent device can typically be used as a vessel prosthesis, which can be obtained in a simple manner by the tubular member supporting a tubular graft material that is resilient or flexible in the longitudinal direction of the tubular member. The flexibility of the graft material allows stretching or spreading of the material on the outside of a curve of the tubular member.

In an embodiment that can be radially compressed to a very small diameter allowing percutaneous insertion by means of the. Seldinger technique of stent devices with a relatively large diameter in the expanded state, the connecting members have a length, keeping the cylindrical spring members at a mutual distance when the tubular member is in its uncompressed state with the larger diameter, and the graft material has annular bellows folds in the areas between the spring members. The extra graft material to be used on the outside of the curves is lying in the areas between the spring members when the device is in its compressed state, and these areas otherwise only have to provide space for the sections of the connecting members that extend between the spring members. To obtain the most compact compression, the graft material is preferably substantially free of bellows folds at the spring members.

It is also possible to give the graft material the requisite flexibility in that the threads of the graft material extending in the longitudinal direction of the tubular member are made of textured yarn while its threads extending in the circumferential direction of the tubular member are made of straight yarn and limit the largest diameter of the tubular member in its uncompressed state. Thus, the annular threads serve to absorb the spring forces from the spring members when they are expanded to the full diameter with such a limitation of the largest diameter, the spring members may be given a relatively heavy design providing suitably large expansion forces, which may be useful, for example, at vessel-opening applications at stenoses, while the vessel wall is kept free of further load if the spring members expand to the full diameter, where the annular threads are fully extended.

BRIEF DESCRIPTION OF THE DRAWING

Examples of embodiments of the invention will now be described in more detail below with reference to the highly schematic drawing, in which.

DETAILED DESCRIPTION OF THE INVENTION

Figure 1:
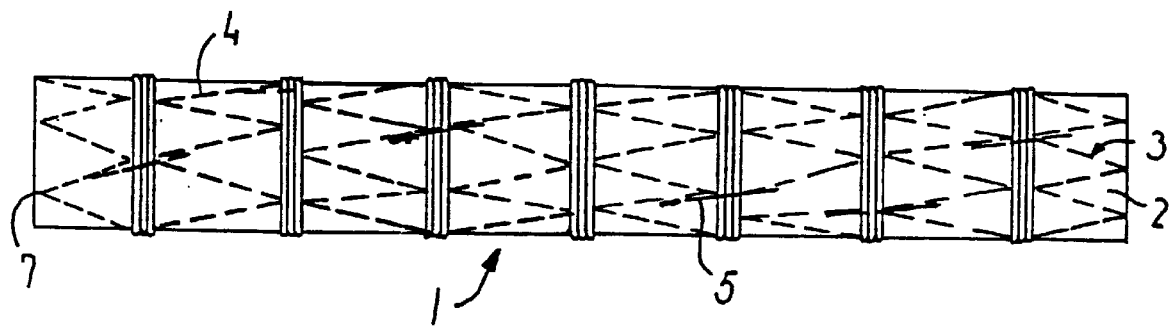
FIG. 1 shows a side view of a preferred embodiment of the stent device.

An endovascular prosthesis shown in FIG. 1 is a preferred embodiment of a stent device 1, which is formed as a single tube, but might just as well have been formed as a branched structure, such as a Y-shaped structure with a relatively large tube branching into two slightly smaller tubes. The latter design can be used, for example, for minimum-invasion treatment of an abdominal aorta aneurysm, while the design with a single tube can be used for treatment of a single-lumen vessel, such as to recreate the lumen of the vessel at a stenosis, for use as a vessel prosthesis at an aneurysm or a fistula or at some other vessel anomaly.

The stent device 1 comprises a graft 2 supported by a tubular member 3, which is constructed from many cylindrical spring members 4 interconnected by connecting members 5.

Figure 2:
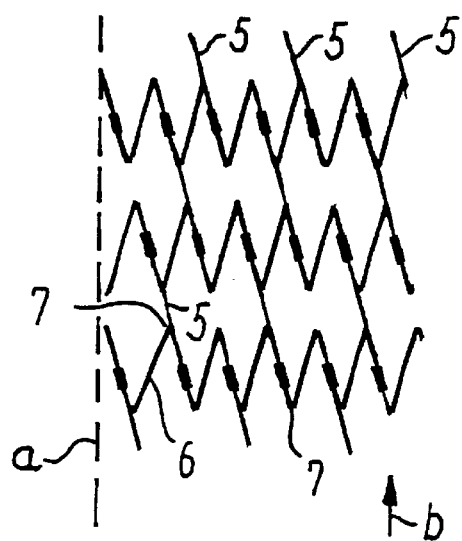
FIG. 2 is a cut open and unfolded view of a segment of interconnected spring members in the device.

The individual spring members 4 are Z-stents of a well-known design made of a wire of stainless steel or nitinol. The wire is bent in a zigzag configuration extending in a cylindrical surface, and the wire ends are joined together to make it endless, and the cylindrical spring member is closed. FIG. 2 shows three spring members which are cut open along the line a and unfolded to a plane shape for the sake of clarity. The longitudinal direction of the tubular member is indicated by the line section b. It should be noted that the different figures use the same reference numerals for details of the same type.

Figure 5:
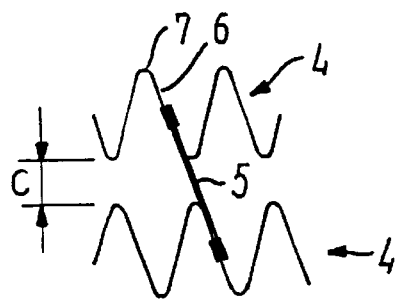
FIGS. 5–7 are enlarged segments around a spring member in the device outlined in an unloaded state, at an axial pressure load and at an axial tensile load, respectively.

The spring member 4 has arm sections 6 each extending between two elbow sections 7. The arm sections are shown as approximately straight in their unloaded state, which is preferred to obtain high axial pressure rigidity, but they may also be made curved. The elbow sections are shown as simple bends in which the wire extends in a single angle of a suitable radius of curvature. Preferably, however, the elbow sections have a more complex design in which the wire at the end of the arm section is bent in an Ω-like course, for example as shown in FIG. 5 in EP-A1 0539237.

As shown in FIG. 2, the connecting members 5 extend obliquely in relation to the longitudinal direction b of the member 1, and in the unfolded state the connecting members are seen to extend largely in parallel with the arm section b and also mutually in parallel. In the cylindrical shape of the member 1, this corresponds to helical courses mutually displaced in parallel in the longitudinal direction b.

The arm sections with associated connecting members can be manufactured as unbroken wire courses along the entire helix, which may be desirable in terms of manufacturing, but this is only possible if the connecting members have substantially less rigidity than the arm sections so that the connecting members can deflect sideways when the tubular member is bent. However, the interrupted course shown in FIG. 2 is often preferred, in which a space follows a pair of interconnected arm sections and then comes another pair of interconnected arm sections, seen in the direction of the helix. In the space the elbow sections are free to be moved closer to or further away from each other.

Figure 3:
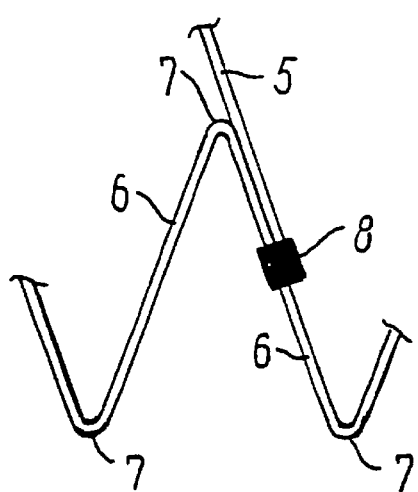
FIG. 3 is an enlarged segment showing a connecting member fastened to an arm section in a spring member.

At their ends the connecting members 5 are firmly fastened to the associated arm sections 6. FIG. 3 shows that the fastening point 8 is at a distance from the elbow sections 7. The fastening may be performed, for example, by means of soldering, welding and/or geometrical locking with mutual geometrical engagement between the connecting member and the arm section. Fastening of this type is performed at both ends of the connecting member. Naturally, the connection may also be made in other places, such as a distance away from the end sections of the connecting member. In the case where the connecting members along a helix are connected through a single, suitably soft, joint wire, the wire is firmly fastened to the arm sections at at least one position at each of the desired arm sections. The point of fastening must be at a distance from the elbow sections, but need not be approximately at the middle of the arm section as shown in FIG. 3. It is thus possible to locate the point of fastening at an interval from 10 to 50 per cent of the distance of the arm section from the nearest elbow section.

Figure 4:
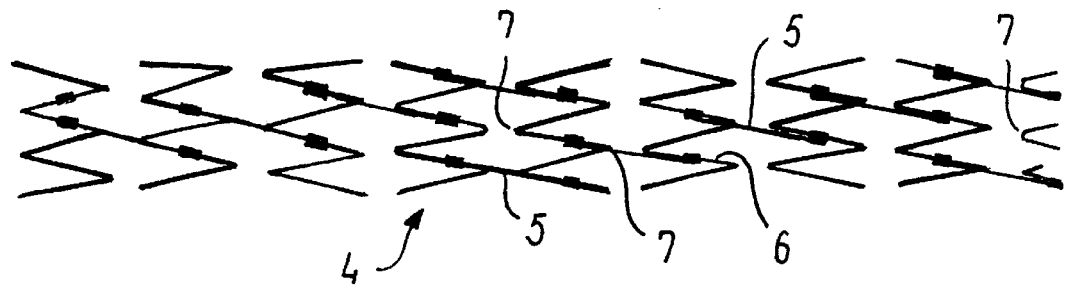
FIG. 4 is a plane view of one half of a stent device shown without graft material.
Figure 6:
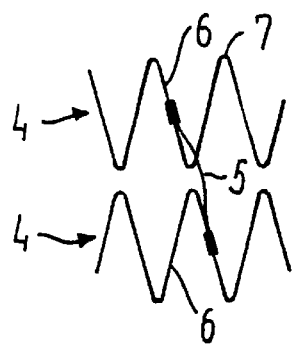
Figure 7:
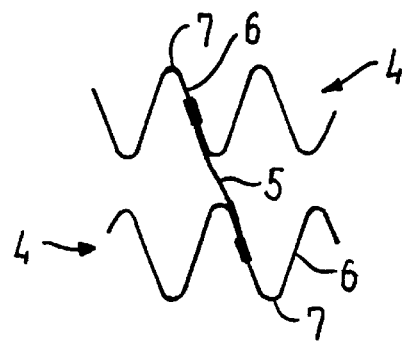

In case of the advantageous locations of the connecting members 5 shown in FIG. 4, between each of the arm sections having a mounted connecting member 5 there is seen to be an arm section without any connecting member. Thus both in the circumferential direction and in the longitudinal direction there is a free elbow section. With this open structure, the individual spring members can be resiliently deformed as indicated in FIGS. 5–7. FIG. 5 shows the approximately unloaded state in which the spring members 4 are kept separated at the mutual distance c by means of the connecting member 5. The distance c can freely be adapted to the specific application by choice of a suitable length of the members 5. It is often advantageous if the distance c is in the range of 2.5 to 100 per cent, suitably from 5 to 30 per cent, of the diameter of the tubular member in its fully expanded state, as the spring members are then located at a suitable closeness to provide a reasonably even support of the vessel, and at the same time there is space between the spring members to absorb graft material and for mutual displacement of the members.

FIG. 6 shows the situation where the spring members are pressure influenced in the longitudinal direction a (the inside of a curve). It can be seen that the connecting member deflects in its transverse direction, and that the surrounding elbow and arm sections are deformed so that the adjacent elbow sections are closer to each other. FIG. 7 shows a deformation pattern in which the spring members are influenced by tension in the longitudinal direction (the outside of a curve). The connecting member 5 cannot be pulled longer, but a deformation occurs of the surrounding elbow and arm sections so that the adjacent elbow sections are further away from each other, which provides an extension of the surface of the tubular member.

Figure 8:
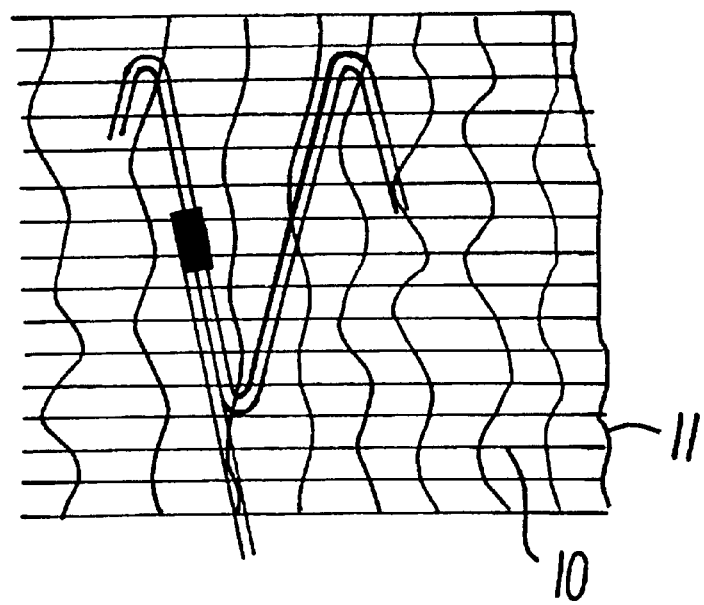
FIG. 8 is an enlarged outline showing graft material with axially textured threads.

When the stent device comprises graft material, the latter may be resilient or elastic in the longitudinal direction. This can be obtained by weaving the graft material from threads, the annular threads 10 (FIG. 8) extending in the circumferential direction being of straight yarn, and the longitudinal threads 11 extending in the longitudinal direction being of textured yarn, that is, the yarn has a wave-shaped course allowing the graft material to stretch in the longitudinal direction. The graft material may suitably be made of polyester. As an alternative to the use of textured yarn, it is possible to use a graft made of a PTFE material in itself being elastic, or a similar commonly used graft material.

Figure 9:
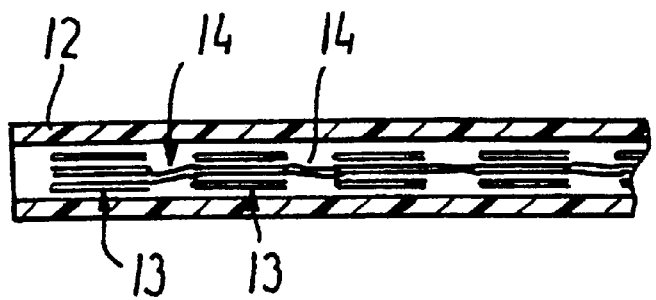
FIG. 9 is a segment of a stent device arranged in an introducer sheath.

Alternatively, the graft material may be bellows-shaped in the areas between the spring members, see FIG. 1. This is advantageous because the extra graft material used at the extension is not located radially opposite to the spring members when the stent device is compacted to its radially compressed state inside an introducer sheath 12. FIG. 9 indicates that the actual wires for the spring members and the connecting members are compacted to a tight pile 13 at the spring members, and that these piles are separated by more open areas 14 in which the few connecting members pass to the next pile 13. The bellows folds are placed directly in the open areas 14 at the compression.

Within the scope of the claims details from the above mentioned embodiments can be combined into other embodiments, and other modifications are possible, such as making the spring members and/or connecting members of other materials than stainless steel or nitnol, e.g. of a resilient plastics material or a metallic material or composite which can exhibit elastic or superelastic properties.

What is claimed is:

1. A stent device comprising:
    at least one tubular member which has a longitudinal direction and several longitudinally consecutive cylindrical spring members interconnected by connecting members, each individual cylindrical spring member being an endless wire of a zigzag configuration having arm sections extending between elbow sections, and the tubular member being self-expanding from a radially compressed state with a relatively small diameter to a state with a larger diameter, wherein between each individual cylindrical spring member and a succeeding cylindrical member in the longitudinal direction, there are at least three resilient connecting members each of which is firmly fastened to only one of the arm sections in an individual cylindrical spring member and to only one of the arm sections in the succeeding cylindrical spring member at a distance from the elbow sections.

2. A stent device according to claim 1, wherein the resilient connecting members extend obliquely in relation to the longitudinal direction when the tubular member is in its uncompressed state with the larger diameter.

3. A stent device according to claim 1, wherein each of the connecting members and the only one arm sections to which it is fastened extend only in the same direction, so that each of the connecting members and the only one arm sections to which it is fastened will extend along several substantially helical courses in the tubular member when the tubular member is in its uncompressed state with the larger diameter.

4. A stent device according to claim 3, wherein the helical courses turn in the same direction.

5. A stent device according to claim 1, wherein the connecting members between adjacent cylindrical spring members are evenly distributed in the circumferential direction.

6. A stent device according to claim 5, wherein with respect to each of the cylindrical spring members, the connecting members to the preceding cylindrical spring member are fastened to arm sections which are positioned at least one arm section offset from the arm sections to which the connecting members are fastened to the succeeding cylindrical spring member.

7. A stent device according to claim 1, wherein each of the connecting members is fastened substantially at the middle of the only one arm sections.

8. A stent device according to claim 1, wherein the connecting members are made of a more flexible spring material than the cylindrical spring members.

9. A stent device according to claim 1, wherein the tubular member supports a tubular graft material that is resilient or flexible in the longitudinal direction of the tubular member.

10. A stent device according to claim 9, wherein the connecting members have a length sufficient to keep the cylindrical spring members at a mutual distance when the tubular member is in its uncompressed state with the larger diameter, the graft material has annular bellows folds in the areas between the spring members, and the graft material is substantially free of bellows folds at the spring members.

11. A stent device according to claim 10, wherein threads of the graft material extending in the longitudinal direction of the tubular member are of textured yarn while threads extending in the circumferential direction of the tubular member are of straight yarn and limit the largest diameter of the tubular member in its uncompressed state.

* * * * *